US009486362B2

(12) United States Patent
Shikamura et al.

(10) Patent No.: US 9,486,362 B2
(45) Date of Patent: Nov. 8, 2016

(54) RING-SHAPED DEVICE (75) Inventors: Yuko Shikamura, Hyogo (JP); Takao Sato, Tokyo (JP); Toru Matsunaga, Tokyo (JP); Yoshiko Yamazaki, Tokyo (JP); Tsutomu Fukushima, Tokyo (JP)

(73) Assignees: Senju Pharmaceutical Co., Ltd., Osaka (JP); SEED Co., Ltd., Tokyo (JP)

( * ) Notice: Subject to any disclaimer, the term of this patent is extended or adjusted under 35 U.S.C. 154(b) by 1009 days.

(21) Appl. No.: 13/146,614

(22) PCT Filed: Dec. 25, 2009

(86) PCT No.: PCT/JP2009/071535
§ 371 (c)(1),
(2), (4) Date: Oct. 14, 2011

(87) PCT Pub. No.: WO2010/092735
PCT Pub. Date: Aug. 19, 2010

(65) Prior Publication Data
US 2012/0022473 A1    Jan. 26, 2012

(30) Foreign Application Priority Data

Feb. 10, 2009  (JP) .................................. 2009-028976
Sep. 30, 2009  (JP) .................................. 2009-228303

(51) Int. Cl.
| A61F 9/04 | (2006.01) |
| A61F 9/00 | (2006.01) |
| A61F 9/06 | (2006.01) |
| A61M 35/00 | (2006.01) |
| A61H 33/04 | (2006.01) |

(52) U.S. Cl.
CPC ............... *A61F 9/04* (2013.01); *A61F 9/0017* (2013.01)

(58) Field of Classification Search
CPC ......... A61M 35/00; A61H 33/04; A61F 9/04
USPC ........................ 604/294, 295, 300, 301, 302
See application file for complete search history.

(56) References Cited

U.S. PATENT DOCUMENTS 4,014,335 A *  3/1977 Arnold .......................... 424/427
6,093,868 A    7/2000 Sawano et al.
(Continued)

FOREIGN PATENT DOCUMENTS

| CN | 101198364 A | 6/2008 |
| JP | H11-151263 A | 6/1999 |
| JP | 2004-521682 A | 7/2004 |

(Continued)

OTHER PUBLICATIONS

Japanese Patent Office, International Search Report in International Application No. PCT/JP2009/071535 (Feb. 23, 2010).

(Continued)

*Primary Examiner* — Michele M Kidwell
*Assistant Examiner* — Ilya Treyger
(74) *Attorney, Agent, or Firm* — Leydig, Voit & Mayer, Ltd.

(57) ABSTRACT

The present invention aims to provide a ring-shaped device superior in the wearing comfort and intraocular stability while being worn on the eye.
Provided is a ring-shaped device to be worn on the scleral surface, which is characterized in that it has an opening to expose the cornea and an intermediate portion between an inner edge portion and an outer edge portion has a maximum thickness.

6 Claims, 3 Drawing Sheets

(56) References Cited

U.S. PATENT DOCUMENTS

| | | | |
|---|---|---|---|
| 7,985,208 B2 * | 7/2011 | Christensen | A61F 2/14 424/428 |
| 2006/0142706 A1 | 6/2006 | Roy et al. | |

FOREIGN PATENT DOCUMENTS

| | | |
|---|---|---|
| JP | 2006-526449 A | 11/2006 |
| JP | 2007-167358 A | 7/2007 |
| RU | 2 344 795 C1 | 1/2009 |
| WO | WO 02/060495 A1 | 8/2002 |
| WO | WO 2006/113377 A2 | 10/2006 |
| WO | WO 2007/038126 A1 | 4/2007 |
| WO | 2008/118938 A1 | 10/2008 |
| WO | 2009/009563 A2 | 1/2009 |

OTHER PUBLICATIONS

Chinese Patent Office, Office Action in Chinese Patent Application No. 200980156513.9 (Jan. 5, 2013).

Japanese Patent Office, Office Action in Japanese Patent Application No. 2010-550422 (Dec. 17, 2013).

* cited by examiner

RING-SHAPED DEVICE

TECHNICAL FIELD

The present invention relates to a ring-shaped device, and particularly to a ring-shaped device superior in the wearing comfort and intraocular stability.

BACKGROUND ART

When a drug is administered by instillation to the eye, a therapeutically effective concentration of the drug can be generally transferred comparatively easily into anterior ocular tissues such as cornea, aqueous humor and the like and external ocular tissues such as lacrimal fluid, conjunctiva and the like. However, it is difficult to transfer a drug to posterior ocular tissues such as retina, choroid, sclera, vitreous body and the like, which are located posterior to the crystalline lens, by instillation to the eye. In addition, oral administration, intravenous injection and the like can be employed as administration methods of a drug to posterior ocular tissues. However, since they are used for systemic administration where a drug is delivered to posterior ocular tissues via systemic circulation of blood, side effects at the site other than the target tissue are feared.

As a new form for intraocular administration of an ophthalmic pharmaceutical agent, patent document 1 proposes an intraocular medicament administration device wherein a flat plane formed from a hydrogel material has a ring shape. However, since the intraocular medicament administration device has a flat shape, stable wearing thereof in the interior of the eye is difficult.

In addition, patent document 2 proposes a ring-shaped device designed to fit the curvature of the eye, which contains a biocompatible material and an ophthalmic drug. The ring-shaped device is placed on the ocular surface without covering cornea but surrounding the cornea and covering a surgery incision site on the sclera in the anterior eye region, and the drug is released from the device to the sclera incision site. However, the intraocular stability while being worn on the eye cannot be afforded only by considering the eye curvature.

In addition, there is no report on the delivery of a drug in a drug-containing ring-shaped device to posterior ocular tissues using the device.

PRIOR ART DOCUMENTS

Patent Documents patent document 1: JP-A-2007-167358
patent document 2: WO2008/118938

SUMMARY OF THE INVENTION

Problems to be Solved by the Invention

The present invention aims to provide a ring-shaped device superior in the wearing comfort and intraocular stability while being worn on the eye. In addition, the present invention aims to provide a ring-shaped device capable of efficiently delivering a drug to posterior ocular tissues.

Means of Solving the Problems

The present inventors have found that a ring-shaped device having a shape wherein an intermediate portion between an inner edge portion and an outer edge portion has a maximum thickness is superior in the wearing comfort and intraocular stability while being worn on the eye. In addition, they have found that a drug can be efficiently delivered to posterior ocular tissues when a ring-shaped device containing the drug is worn on the scleral surface.

Accordingly, the present invention provides the following.

(1) A ring-shaped device to be worn on the scleral surface, which has an opening to expose the cornea and an intermediate portion between an inner edge portion and an outer edge portion, wherein the intermediate portion has a maximum thickness.
(2) The ring-shaped device of (1), wherein the inner edge portion has a thickness of 0.3 mm or below, the outer edge portion has a thickness of 0.3 mm or below, and the intermediate portion has a thickness of 0.4 mm or below.
(3) The ring-shaped device of (1), wherein the inner edge portion has a thickness within the range of 0.1-0.3 mm, the outer edge portion has a thickness within the range of 0.15-0.3 mm, and the intermediate portion has a thickness within the range of 0.2-0.4 mm.
(4) A ring-shaped device comprising a drug and capable of delivering the drug to posterior ocular tissues by being worn on the scleral surface, which device having an opening to expose the cornea.
(5) The ring-shaped device of (4), comprising an intermediate portion having a maximum thickness between an inner edge portion and an outer edge portion.
(6) The ring-shaped device of (5), wherein the inner edge portion has a thickness of 0.3 mm or below, the outer edge portion has a thickness of 0.3 mm or below, and the intermediate portion has a thickness of 0.4 mm or below.
(7) The ring-shaped device of (5), wherein the inner edge portion has a thickness within the range of 0.1-0.3 mm, the outer edge portion has a thickness within the range of 0.15-0.3 mm, and the intermediate portion has a thickness within the range of 0.2-0.4 mm.
(8) A method of transferring a drug contained in a ring-shaped device to posterior ocular tissues, comprising applying the device on the scleral surface, which device having an opening to expose the cornea.

Effect of the Invention

According to the present invention, a ring-shaped device superior in the wearing comfort and intraocular stability while being worn on the eye, and permitting long-term wearing can be provided. Moreover, when a ring-shaped device containing a drug is applied on the scleral surface, the drug can be efficiently delivered to posterior ocular tissues. Since long-term wearing is possible, a sufficient amount of a drug can be delivered to posterior ocular tissues.

BRIEF DESCRIPTION OF THE DRAWINGS

FIG. 3 (A) and (B) are plane views of another embodiment of the ring-shaped device of the present invention.

MODE OF PRACTICING THE INVENTION

The present invention is explained in the following by referring to preferable embodiments.

The ring-shaped device of the present invention is to be worn on the scleral surface and is mainly characterized in that it has an opening to expose the cornea and an intermediate portion between an inner edge portion and an outer edge portion has a maximum thickness.

The ring-shaped device of the present invention comprising the intermediate portion having the maximum thickness between the inner edge portion and the outer edge portion permits long-term wearing since it affords superior wearing comfort and intraocular stability while being worn on the eye. In addition, when such ring-shaped device containing a drug is applied on the scleral surface, the drug in the device can be efficiently delivered to posterior ocular tissues.

Shape and Size of Device

Figure 1:
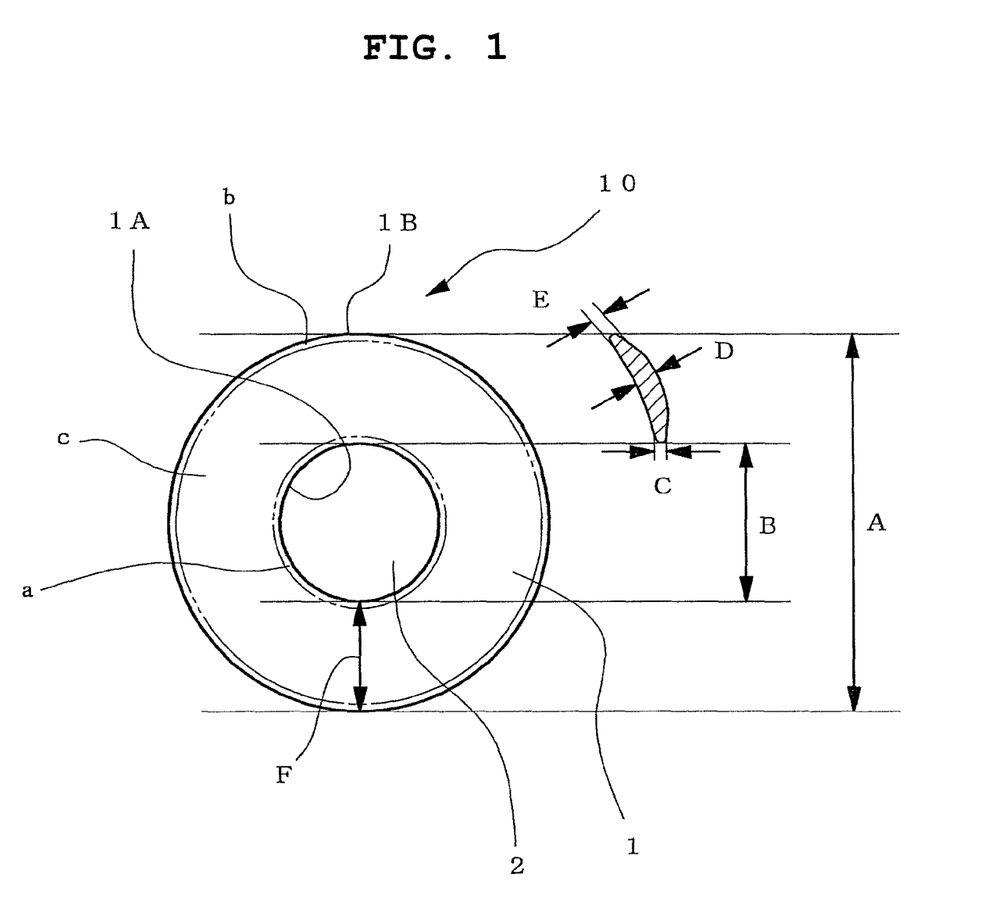
FIG. 1 is a plane view and a sectional view of one embodiment of the ring-shaped device of the present invention.

FIG. 1 is a plane view and a sectional view of one embodiment of the ring-shaped device of the present invention. The ring-shaped device of the present invention comprises, as shown in device 10 in said embodiment, a curved thin film 1 having an opening (penetrating hole) 2 to expose the cornea, wherein one surface of the curved thin film forms a concave surface and another surface of the curved thin film forms a convex surface.

While the planar shape (i.e., outline of outer circumference of curved thin film) of the device is not particularly limited, it is preferably substantially circular like device 10 of the above embodiment, so that the about entirety of the scleral surface can be uniformly covered by the device. Here, the "substantially circular" is not limited to the about true circle shown in FIG. 1, but includes ellipse and elongated ellipse as long as convenient wearing of a ring-shaped device on the eye and wearing comfort thereof are not significantly influenced. Also, it is not limited to a curved thin film 1 having a strictly circular arc of the outline, but includes a curved thin film 1 having a roughly circular outline which may partly contain a wavy line, a zigzag line, a straight line and the like.

The size of the ring-shaped device of the present invention is not particularly limited as long as it can be worn with ease and can cover the scleral surface. When, for example, the ring-shaped device is comprised of a curved thin film 1 having an about circular outline of the outer circumference, as shown in device 10 of FIG. 1, an outer diameter A thereof is preferably about 16-20 mm, more preferably about 18-20 mm, to facilitate insertion of the device in the eye (easiness of wearing) and to cover the scleral surface with the device. An inner diameter B thereof (size of opening 2) is preferably about 10-15 mm, more preferably about 12 mm, to simultaneously achieve prevention of the ring-shaped device from being in contact with the cornea (corneal exposure) and long-term wearing.

Considering the wearing comfort and intraocular stability of the ring-shaped device of the present invention while being worn on the eye, an intermediate portion between an inner edge portion and an outer edge portion has the maximum thickness. Here, the inner edge portion refers to a part having any width within 0.5 mm (preferably 0.3-0.5 mm, more preferably 0.3 mm) along the inner circumference 1A on the opening 2 side of the curved thin film 1 (symbol a in the plane view of FIG. 1), the outer edge portion refers to a part having any width within 0.5 mm (preferably 0.3-0.5 mm, more preferably 0.3 mm) along the outer circumference 1B of the curved thin film 1 (symbol b in the plane view of FIG. 1), and the intermediate portion refers to the remaining part excluding the inner edge portion a and the outer edge portion b (symbol c in the plane view of FIG. 1).

In the ring-shaped device of the present invention, "the intermediate portion has the maximum thickness" means that a maximum thickness portion of the ring-shaped device (curved thin film 1) is formed in an intermediate portion c. Here, the position of formation of the maximum thickness portion is not particularly limited as long as it is in the intermediate portion c. However, it is essential that the maximum thickness portion be formed on the side of the central portion of curved thin film 1 (i.e., position equally dividing the width of curved thin film 1 (size F in FIG. 1)), rather than the side of the border between the inner edge portion and the intermediate portion and the side of the border between the intermediate portion and the outer edge portion, and it is preferably formed near the central portion. Here, the "near the central portion" includes positions within 0.5 mm from the position equally dividing accurately the width of curved thin film 1 (size F in FIG. 1).

In the ring-shaped device of the present invention, the thickness of the inner edge portion a is generally set to not more than 0.3 mm, preferably within the range of 0.05-0.3 mm, more preferably within the range of 0.1-0.3 mm, particularly preferably within the range of 0.13-0.23 mm, and the thickness of the outer edge portion b is generally set to not more than 0.3 mm, preferably within the range of not more than 0.05-0.3 mm, more preferably within the range of 0.15-0.3 mm, particularly preferably within the range of 0.17-0.23 mm. Both the inner edge portion a and the outer edge portion b may be formed to have a substantially uniform thickness. Typically, however, as shown in FIG. 1, the inner edge portion a is formed to have an increasing thickness from the inner circumference 1A to the intermediate portion c of the curved thin film 1, and the outer edge portion b is formed to have an increasing thickness from the outer circumference 1B to the intermediate portion c of the curved thin film 1.

The thickness of the intermediate portion c having the maximum thickness portion is generally set to not more than 0.4 mm, preferably within the range of 0.08-0.4 mm, more preferably within the range of 0.2-0.4 mm, particularly preferably within the range of 0.33-0.38 mm, and the thickness of the maximum thickness portion in the intermediate portion c is preferably greater by 0.03 mm or more than both the maximum thickness of the inner edge portion and the maximum thickness of the outer edge portion.

With a ring-shaped device (curved thin film 1) with an intermediate portion having the maximum thickness between an inner edge portion and an outer edge portion, an influence on the eyelid pressure due to eyeblink can be minimized, whereby misalignment of the device inside the eye and dropout thereof can be prevented. Since a shape preferable for the ring-shaped device can be retained and folding of the device inside the eye due to eyeblink can be prevented, long-term wearing is possible. Moreover, since the device is superior in handling, intraocular insertion is easy.

Moreover, by setting the thickness of the inner edge portion, the outer edge portion and the intermediate portion to fall within the above-mentioned ranges, misalignment of the device inside the eye can be further prevented, a contact between the ring-shaped device and the cornea can be prevented, and a foreign-body sensation caused by the contact between the ring-shaped device and the cornea can be reduced, thus enabling longer-term wearing.

Opening 2 in the ring-shaped device of the present invention exposes the cornea. Therefore, an opening 2 is preferably formed so that a curved thin film 1, which is the substance of the ring-shaped device, will not touch the cornea while it is worn on the eye. By forming an opening 2 that exposes the cornea, a foreign-body sensation caused by the contact between the ring-shaped device and the cornea can be reduced. When a ring-shaped device contains a drug, particularly a therapeutic agent for posterior ocular tissue diseases, the opening suppresses transfer of the drug released from the ring-shaped device to external ocular tissues such as lacrimal fluid and the like and anterior ocular tissues such as cornea, aqueous humor and the like, thereby enabling delivery of a greater amount of the drug to posterior ocular tissues. In addition, it does not lower the visual acuity. Thus, the shape of the opening 2 is generally preferably about true circle corresponding to the cornea as shown in FIG. 1. As long as corneal exposure is not prevented, a shape other than about true circle is also acceptable. The position of the opening 2 is generally about center of a ring-shaped device (curved thin film 1), as shown in FIG. 1. When the shape of a ring-shaped device as a whole is adjusted so that the opening will fit the cornea when a ring-shaped device is worn on the eye, the position of the opening 2 does not need to be about center of the curved thin film 1, but may be eccentrically-located on one side of the outer edge of the curved thin film 1.

The ring-shaped device of the present invention preferably has a ring shape like the device 10 in FIG. 1, wherein the shaft center of the curved thin film 1 and that of the opening 2 are about concentric, and the width of the curved thin film 1 (width of planar view: size F in FIG. 1) varies within the range of 5 mm or below over the entire circumference of the ring-shaped device, from the aspects of easiness of wearing on the eye and fitting of the opening to the cornea during wearing.

The base curve (BC) of the curved thin film 1 in the ring-shaped device is appropriately determined from the curvature of the sclera, and is generally 8.8-13 mm, preferably 10-12 mm.

Figure 3:
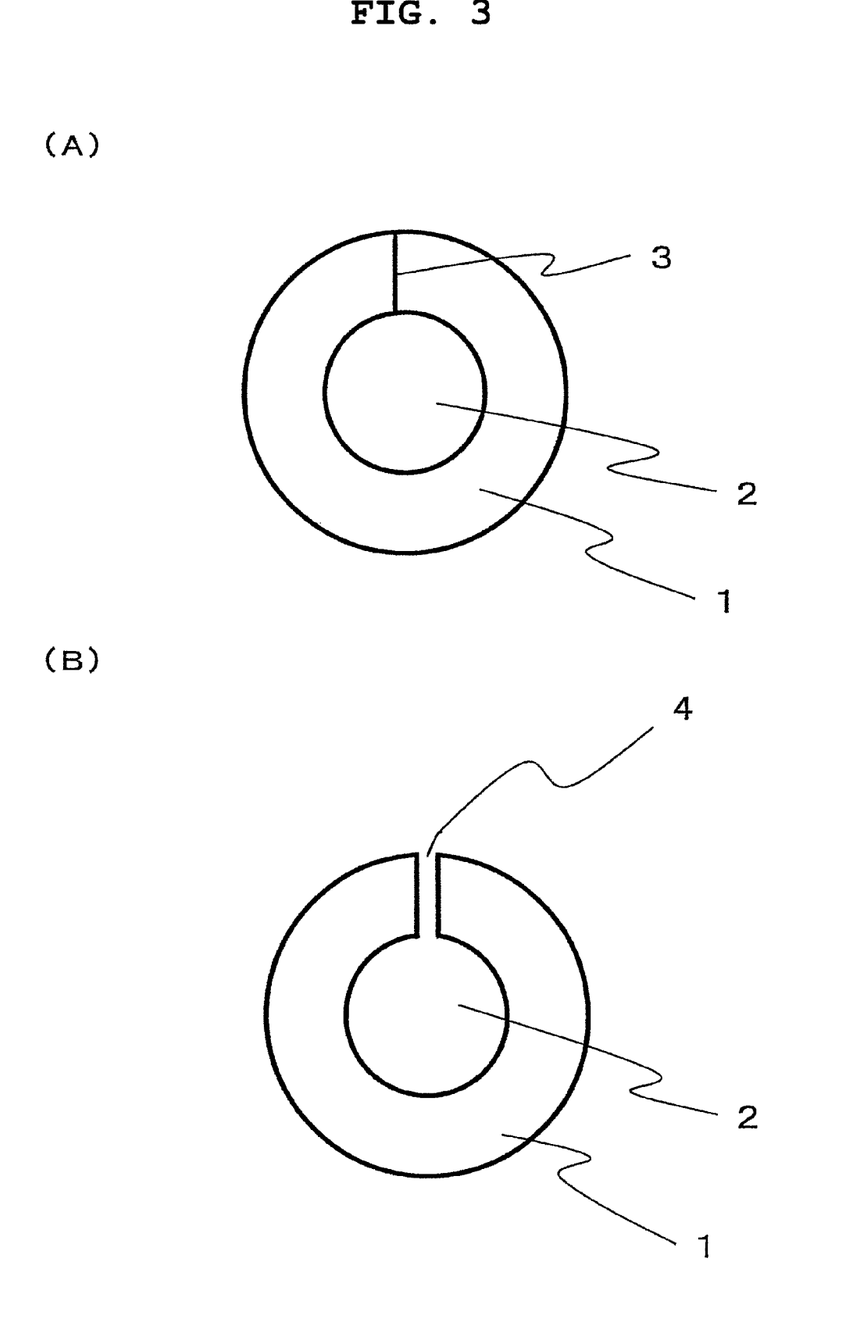

In the present invention, the ring-shaped device may have a cut 3 (FIG. 3(A)) or a clipping portion 4 (FIG. 3(B)), which divides the ring-shaped curved thin film 1, in order to improve easiness of wearing on the eye, handling of the device and the like.

Material of Ring-shaped Device

The ring-shaped device of the present invention is comprised of a hydrogel. Examples of the hydrogel include hydrogel produced by using a hydrophilic monomer, and a hydrogel produced by adding a hydrophobic monomer or a crosslinkable monomer or the both to a hydrophilic monomer.

Hydrophilic monomer enables enhancement of the water content ratio, and hydrophobic monomer enables control of the water content ratio, rate of swelling and the like of the obtained hydrogel, as well as fine control of drug dose when the device contains a drug. Crosslinkable monomer enables, depending on its content, control of the polymer chain density of hydrogel. By controlling the crosslinking density, drug diffusion can be inhibited, release of the contained drug can be delayed, and the drug release rate can be controlled. In addition, crosslinkable monomer not only controls the drug release rate but can impart hydrogel with mechanical strength, shape stability and solvent resistance.

Here, the water content ratio of hydrogel (water content ratio (wt %)=[(W−D)/W]×100 (W: water-containing weight, D: dry weight)) is preferably 30-70 wt %, which is comparable to the water content ratio of hydrogel contact lenses put into practical use (about 35-70 wt %). When the ring-shaped device contains a drug, an appropriate water content ratio can be determined according to the target drug, since the ingested amount and the release behavior of the drug are important.

Preferable examples of the hydrophilic monomer include those having one or more hydrophilic groups in the molecule, such as 2-hydroxyethyl (meth)acrylate, 2-hydroxymethyl (meth)acrylate, hydroxypropyl (meth)acrylate, glycerol (meth)acrylate, acrylamide, N,N-dimethyl (meth)acrylamide, N,N-diethyl (meth)acrylamide, N-vinylpyrrolidone, diacetone acrylamide, N-vinyl acetamide, (meth)acrylic acid, (meth)acryloxyethyl succinate, itaconic acid, methacrylamidopropyl triammonium chloride, 2,3-dihydroxypropyl (meth)acrylate and the like. Among these, two or more kinds of hydrophilic monomers may be used in combination. In addition, from among the above-mentioned hydrophilic monomers, 2-hydroxyethyl (meth)acrylate is preferable.

When the ring-shaped device contains a drug, moreover, a hydrophilic monomer to be used needs to be appropriately selected depending on the structure, release time and release amount of the employed drug. For example, when an ionic drug is selected, a monomer having an ionic group to be a counter ion is selected as a hydrophilic group, since the drug can be strongly retained in the hydrogel due to ion binding. In addition, since release of a drug is also influenced by a water content ratio, a monomer having strong hydrophilicity such as ionic group and the like needs to be selected to obtain a hydrogel with a high water content ratio, and a monomer having somewhat weaker hydrophilicity such as hydroxyl group and the like needs to be selected to obtain a hydrogel with a low water content ratio.

Examples of the hydrophobic monomer include siloxanyl (meth)acrylate, trifluoroethyl (meth)acrylate, methacrylamide, cyclohexyl (meth)acrylate, normal-butyl (meth)acrylate and the like. Of these, two or more kinds of hydrophobic monomers may be used in combination.

In addition, when the ring-shaped device contains a drug, the above-mentioned hydrophobic monomer also needs to be appropriately selected depending on the structure, release time and release amount of the employed drug, as in the case of the hydrophilic monomer. For example, when a hydrophobic drug is selected, a hydrophobic monomer can be selected in an attempt to improve compatibility of the hydrophilic monomer and the drug. It is also possible to change the water content ratio of the obtained hydrogel, depending on the content of the hydrophobic monomer. However, when the content of the hydrophobic monomer exceeds 90 wt % relative to the total monomer content, the water content ratio decreases extremely, possibly eliminating use thereof as a hydrogel. Thus, the upper limit is preferably not more than 90 wt % relative to the total amount of the monomers.

Examples of the crosslinkable monomer include ethylene glycol di(meth)acrylate, methylenebisacrylamide, 2-hydroxy-1,3-dimethacryloxypropane, trimethylolpropane triacrylate and the like. From these, two or more kinds of the crosslinkable monomers may be used in combination.

The content of the crosslinkable monomer is preferably 0.1-40 wt %, particularly preferably 0.1-10 wt %, relative to the total amount of monomers in view of a shape adjustment effect of a polymer gel. When the content is less than 0.1 wt %, the polymer gel contains insufficient amount of a mesh structure, and when it exceeds 40 wt %, the polymer gel contains redundant mesh structure, thus providing a brittle polymer gel.

Examples of the polymerization initiator to be used for polymerizing a mixture of these monomers include general radical polymerization initiators such as peroxides (e.g., lauroyl peroxide, cumene hydroperoxide, benzoyl peroxide and the like), azo-bis-valeronitrile, azo-bis-isobutyronitrile and the like. The amount of the polymerization initiator to be added is preferably about 10-3500 ppm relative to the total amount of the monomers.

Drug

The ring-shaped device of the present invention can contain a drug. As such drug, a drug that can be dissolved in a solvent is used, which is preferably a drug used for the prophylaxis or treatment of posterior ocular tissue diseases.

The posterior ocular tissue in the present invention means eye tissues located posterior from the crystalline lens, and specifically refers to the sclera, retina-choroid, and vitreous body. Examples of the posterior ocular tissue diseases include postoperative infection, diabetic retinopathy, retinal blood vessel occlusion, pigmentary degeneration of retina, chorioretinal disease, retinal dystrophy, macular dystrophy, macular degeneration, macular edema, retinitis, retinochoroiditis, optic neuritis, optic neuropathy, retinal detachment, optic atrophy, division of the optic nerve and the like. In addition, examples of the agent for the prophylaxis or treatment of posterior ocular tissue diseases include antibacterial agent, steroidal anti-inflammatory agent, non-steroidal anti-inflammatory agent, antiallergic agent, antivirus agent, antifungal agent, angiogenesis inhibitor, retinal neurite formation promoter, retinal neuroprotective agent, optic nerve regeneration promoter, optic nerve protector and the like.

In the present invention, the ring-shaped device can be made to contain a drug by, for example, dissolving a desired drug to give a drug solution, and immersing the ring-shaped device in the drug solution. Examples of the solvent in which a drug is to be dissolved include water, hydrophilic solvents, a mixed solvent of water and a hydrophilic solvent and the like, and examples of the hydrophilic solvent include ethanol, methanol, isopropanol, n-butanol, dimethylformamide and the like. While the drug concentration of the drug solution is determined according to the amount of the drug to be contained in the ring-shaped device, it is generally $5.0 \times 10^{-9}$-$10^{-2}$ mol/L. When ofloxacin is used as an antibacterial agent, the concentration thereof is $1.0 \times 10^{-4}$-$1.0$ mol/L, preferably $5.0 \times 10^{-3}$-$0.5$ mol/L.

While the drug content of the ring-shaped device varies depending on the kind of the drug, therapeutically effective concentration, period of drug release, symptoms and the like, it is generally 0.01-95 wt %, preferably 0.1-30 wt %. When ofloxacin is used as an antibacterial agent, for example, the concentration thereof is generally 0.1-30 wt %, preferably 0.5-15 wt %.

The ring-shaped device of the present invention shows superior intraocular stability, permits long-term wearing on the eye, and can release a drug in the ring-shaped device in a sustained manner.

Production Method of Device

The ring-shaped device of the present invention can be produced according to a casting mold production method or a lathe cutting production method. The casting mold production method includes performing polymerization in a forming mold designed in advance to afford a desired shape (ring shape) after polymerization, whereby a ring-shaped device is produced. The lathe cutting production method includes first forming a block polymer and cutting, polishing and the like the block polymer into a ring-shaped device.

Casting Mold Production Method

First, to a hydrophilic monomer or a mixture of a hydrophilic monomer and a hydrophobic monomer or a crosslinkable monomer, or a mixture of a hydrophilic monomer, a hydrophobic monomer and a crosslinkable monomer is added a polymerization initiator, and the mixture is stirred and dissolved to give a monomer mixture.

The above-mentioned monomer mixture is placed in a forming mold made of metal, glass, plastic or the like, the mold is tightly sealed, and the temperature in a thermostatic tank and the like containing the mold is raised successively or continuously within the range of 25° C.-130° C. for 5-120 hr to complete the polymerization. Ultraviolet ray, electron beam, gamma ray and the like can be used for the polymerization. Alternatively, water and an organic solvent are added to the above-mentioned monomer mixture, and solution polymerization can be performed.

After the completion of the polymerization, the temperature is lowered to room temperature, and the obtained polymer product is taken out from the forming mold and cut and polished as necessary. The obtained device (ring-shaped device) is subjected to hydration and swelling to give a hydrated gel (hydrogel). Examples of the liquid (swelling solution) to be used for hydration and swelling include water, saline, isotonic buffer and the like, and a mixture with a water-soluble organic solvent can also be used. The aforementioned swelling solution is heated to 40-100° C., and the device is immersed for a given time to rapidly achieve a hydrated and swollen state. In addition, the aforementioned swelling treatment can remove unreacted monomer contained in the polymer product.

Lathe Cutting Production Method

First, a block-shaped polymer is obtained in the same manner as in the casting mold production method by using a forming mold affording a block shape after polymerization, and a corneoscleral lens is produced by cutting the block. An opening of a desired size is formed in the obtained corneoscleral lens, and the surrounding portion is polished to give a ring-shaped device. It is also possible to first form an opening and then cut into a lens-like device.

The ring-shaped device of the present invention is worn on a scleral surface, particularly, bulbar conjunctiva covering the scleral surface. An aid exclusive for wearing can also be used. While the dose of a drug by the ring-shaped device of the present invention varies depending on the kind thereof, it is generally about 1 μg-100 mg per dose. In addition, while the administration frequency of a drug by the ring-shaped device of the present invention can be appropriately determined based on the symptom, age and the like, the device may be applied to the eye once to several times (e.g., 1-6 times) a day or once in several days to several months.

EXAMPLES

Experimental Example 1

Production of Ring-shaped Device (Production Method of Ring-shaped Device)

2-Hydroxyethyl methacrylate (99 g) as a hydrophilic monomer, ethylene glycol dimethacrylate (1 g) as a crosslinkable monomer and 2,2'-azo-bis-isobutyronitrile (0.15 g) as a polymerization initiator were mixed, and the mixture was subjected to heating polymerization in a test tube with outer diameter (30 mm) and height (100 mm) (under a nitrogen atmosphere, heated from room temperature to 100° C., for 40 hr). The obtained polymer was taken out from the test tube, cut and polished into a desired shape to give a ring-shaped device before swelling. The obtained device before swelling was swollen by heating at 60° C. for 30 min in saline, and sterilized with high-pressure steam to give a ring-shaped device.

Experimental Example 2

Wearing Comfort and Intraocular Stability Test (Test Method)

According to the method of Experimental Example 1, the ring-shaped devices of Examples 1-3 shown in Table 1 were prepared (water content ratio: each 38 wt %). Similarly, the ring-shaped devices of Comparative Examples 1-2 were prepared (water content ratio: each 38 wt %). The thickness of the devices was measured using DIAL THICKNESS GAUGE (G-1A) manufactured by OZAKI MFG. CO., LTD. As the thickness of the inner edge portion, the thickness at 0.3 mm from the edge portion (inner circumference of curved thin film 1) 1A on the device opening 2 side (C in FIG. 1) was measured, as the thickness of the outer edge portion, the thickness at 0.3 mm from the edge portion (outer circumference of curved thin film 1) 1B on the side opposite from the opening 2 (E in FIG. 1) was measured, and as the thickness of the intermediate portion, the thickness of the central portion (D in FIG. 1) between the edge portion (inner circumference of curved thin film 1) 1A on the device opening 2 side and the edge portion (outer circumference of curved thin film 1) 1B on the side opposite from the opening 2 was measured. The ring-shaped devices of Examples 1-3 and Comparative Examples 1-2 were applied on the eyes of the test subjects and the state of the devices in the eyes was observed with a slit lamp microscope.

Wearing comfort: good wearing comfort wherein the test subject did not feel a foreign body was marked with ○, when a foreign body was somewhat felt but wearing was not prevented thereby, Δ was marked, and the presence of a foreign body of the level preventing wearing was marked with x.

Intraocular stability: when the device was stably held at the center of the eye on eyeblink, ○ was marked, when the device was slightly misaligned but did not reach the pupil, Δ was marked, and when the device was misaligned and dropped or reached the pupil, x was marked.

(Results)

TABLE 1

|  | outer diameter A (mm) | inner diameter B (mm) | thickness (mm) | | | wearing comfort | intraocular stability |
| --- | --- | --- | --- | --- | --- | --- | --- |
|  |  |  | inner edge portion | intermediate portion | outer edge portion |  |  |
| Example 1 | 20 | 14 | 0.23 | 0.33 | 0.23 | ○ | ○ |
| Example 2 | 16 | 10 | 0.18 | 0.38 | 0.18 | ○ | ○ |
| Example 3 | 18 | 12 | 0.13 | 0.34 | 0.17 | ○ | ○ |
| Comparative Example 1 | 20 | 14 | 0.23 | 0.23 | 0.42 | Δ | x |
| Comparative Example 2 | 20 | 14 | 0.29 | 0.29 | 0.29 | ○ | x |

In the ring-shaped devices of Examples 1-3, the intermediate portion (central portion of curved thin film) had the maximum thickness, and all of them were marked with ○ for both the wearing comfort and intraocular stability.

In contrast, in the ring-shaped device of Comparative Example 1, the outer edge portion of the curved thin film had the maximum thickness, and the wearing comfort was Δ. However, since the device was pulled by the eyelid on eyeblink and misaligned in the eye, the stability was x.

In the ring-shaped device of Comparative Example 2, the inner edge portion, the intermediate portion and the outer edge portion of the curved thin film had no distinct difference in the thickness, and the wearing comfort was ○. In a test subject with a high eyelid pressure, however, since the lens was bent and dropped from the eye, the stability was x.

Experimental Example 3

Production of Device (Production Method of Device)

Example 4

Scleral Ring

2-Hydroxyethyl methacrylate as a hydrophilic monomer and ethyleneglycol dimethacrylate as a crosslinkable monomer were mixed such that their concentrations in the resulting monomer mixture were 99.5 wt % and 0.5 wt %, respectively, azo-bis-isobutyronitrile as a polymerization initiator was added to the monomer mixture to 1000 ppm, and the mixture was stirred. The obtained monomer mixture was fed in a polypropylene forming mold (diameter 40 mm, height 50 mm), and polymerized under a nitrogen atmosphere by raising the temperature from room temperature to 100° C. over 40 hr. The obtained polymer product was taken out from the forming mold, cut and polished into a scleral lens shape. The obtained lens was immersed in phosphate buffer (pH 7) at 60° C. for 1 hr for hydration and swelling to give a scleral lens (diameter 20 mm, base curve 11 mm). The central portion of the obtained scleral lens was removed by a trephine (diameter 13.0 mm) to give a ring-shaped device (water content ratio: 38 wt %, outer diameter: 20 mm, inner diameter: 13 mm). The ring-shaped device had an inner edge portion thickness: 0.4 mm, an intermediate portion thickness: 0.35 mm, and an outer edge portion thickness: 0.15 mm (measured in the same manner as in Example 2).

Comparative Example 3

Corneoscleral Lens

The lens before processing of the central portion with a trephine in Example 4 was used as a corneoscleral lens. The corneoscleral lens had a central portion thickness: 0.2 mm, and an outer edge portion thickness: 0.15 mm (measured in the same manner as in Experimental Example 2).

Comparative Example 4

Corneal Lens

The monomer mixture used in Example 4 was fed in a polypropylene forming mold with a corneal lens shape, and the polymerization and hydration and swelling were performed in the same manner as in Example 1 to give a corneal lens having a diameter 13.0 mm (water content ratio: 38 wt %). The corneal lens had a central portion thickness: 0.2 mm, and an outer edge portion thickness: 0.15 mm (measured in the same manner as in Experimental Example 2).

Experimental Example 4

Drug Transferability to Anterior Ocular Tissues and Posterior Ocular Tissues

[Test Device]

Example 4

Scleral Ring

Comparative Example 3

Corneoscleral Lens

Comparative Example 4

Corneal Lens

[Test Method]

Figure 2:
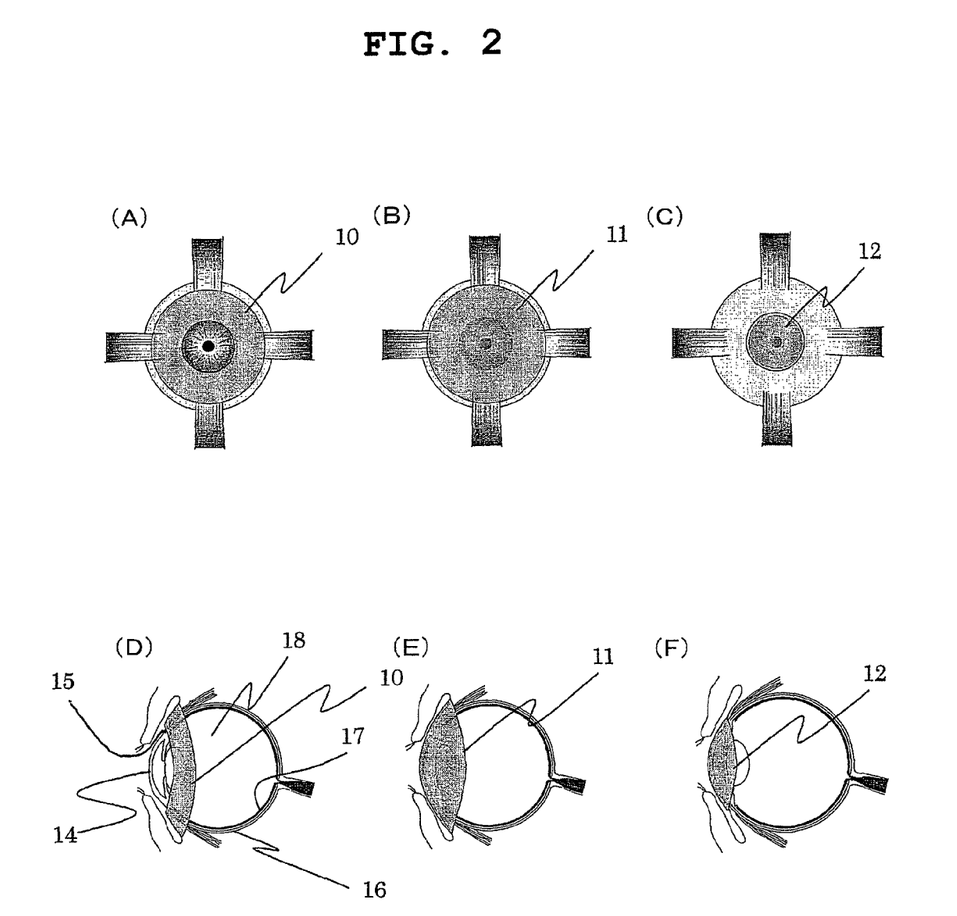
FIG. 2 provides front views (FIG. 2 (A)-(C)) and side views (FIG. 2 (D)-(F)) showing the state of wearing of each device in Experimental Example 4, wherein FIG. 2 (A) and (D) show the state of wearing of the device of Example 4, FIG. 2 (B) and (E) show that of Comparative Example 3, and FIG. 2 (C) and (F) show that of Example 4.

A 0.3% ofloxacin ophthalmic solution (pH 6.5) containing 0.3% ofloxacin and 0.85% sodium chloride was prepared. The devices of Example 4 and Comparative Examples 3 and 4 were immerse in a 0.3% ofloxacin ophthalmic solution (20 mL) and shaken at 100 rpm for 24 hr to impregnate the device with ofloxacin (weight after ofloxacin impregnation: Example 4: 171 mg, Comparative Example 3: 252 mg, Comparative Example 4: 34 mg). The nictating membrane was incised from the eyes of Japanese white rabbits (male, body weight 2-3 kg) and the devices of Example 4 and Comparative Examples 3 and 4 were applied on the eyes. FIG. 2 shows the state of wearing of each device from the front of the eyeball (FIG. 2(A)-(C)) and from the side (FIG. 2(D)-(F)), and FIGS. 2(A) and (D) show the state of wearing of the device of Example 4, FIG. 2(B) and (E) show the state of wearing of the device of Comparative Example 3, and FIGS. 2(C) and (F) show the state of wearing of the device of Comparative Example 4. In the side view of FIG. 2, 14 is cornea, 15 is bulbar conjunctiva, 16 is sclera, 17 is retina-choroid, and 18 is vitreous body. The scleral ring 10 of Example 4 is worn to cover sclera 16, particularly bulbar conjunctiva 15, the corneoscleral lens 11 of Comparative Example 3 is worn to cover cornea 14 and bulbar conjunctiva 15, and the corneal lens 12 of Comparative Example 4 is worn to cover cornea 14.

At 1 hr from wearing, the lacrimal fluid was recovered and the rabbits were sacrificed with an excess amount of 5% pentobarbital sodium. The eyeballs were washed with saline, the aqueous humor was recovered, and the eyeballs were removed and frozen. The cornea and retina-choroid were harvested from the frozen eyeballs. The lacrimal fluid was added with a mobile phase (0.2 mL) to give a sample solution. The aqueous humor was passed through a 0.22 μm filter, and the filtrate was used as a sample solution. The retina-choroid was homogenized with acetonitrile (5 mL), and the homogenate was shaken up and down at 200 rpm for 20 min and centrifuged at 3000 rpm for 10 min. The supernatant (4.5 mL) was transferred to a different test tube, dried under reduced pressure in a rotary evaporator, and dissolved again in mobile phase (0.5 mL). The solution was ultracentrifuged at 12000 rpm for 5 min, and the supernatant was used as a sample solution. A sample solution (10 μL) was measured for ofloxacin concentration (n=2-3) of each tissue under the following HPLC conditions.

Separately, ofloxacin was extracted from the devices of Example 4 and Comparative Examples 3 and 4 immersed in 0.3% ofloxacin ophthalmic solution for 24 hr, and the ofloxacin content of each device was measured.

(Extraction Method)

Each device containing ofloxacin was immersed in methanol (10 mL) and shaken at 100 rpm for 72 hr to extract ofloxacin. This solution was diluted with mobile phase to give a sample solution. The sample solution (10 μL) was measured for the content of ofloxacin in each device under the following HPLC conditions (n=3).

(HPLC Measurement Condition)

detector: spectrofluorometric detector (excitation wavelength: 290 nm, measurement wavelength: 490 nm)
column: Inertsil ODS-3 4.6 mmϕ×150 mm
guard column: Inertsil ODS-3 4.6 mmϕ×5 mm, cartridge type (GL cart)
column temperature: fixed temperature around 38° C.
mobile phase: 40% methanol/5% acetic acid/3 mM sodium octane sulfonate solution
flow rate: 1.0 mL/min
injection volume: 10 μL
sample cooler temperature: 4° C.

[Results]

Table 2 shows the ofloxacin concentration of each tissue as corrected by the content of ofloxacin in each device.

TABLE 2

| | | Example 4 (scleral ring) | Comparative Example 3 (corneoscleral lens) | Comparative Example 4 (corneal lens) |
|---|---|---|---|---|
| | ofloxacin content of device [mg/device] | 1.20 ± 0.019 | 1.72 ± 0.03 | 0.28 ± 0.017 |
| external ocular region | lacrimal fluid [(μg/g-tissue)/(mg/device)] | 208.54 ± 28.61 | 528.17 ± 91.31 | 969.13 ± 223.93 |
| anterior ocular region | cornea [(μg/g-tissue)/(mg/device)] | 10.86 ± 0.35 | 18.21 ± 5.23 | 58.95 ± 2.47 |
| | aqueous humor [(μg/mL-tissue)/(mg/device)] | 3.16 ± 0.34 | 5.11 ± 0.58 | 20.96 ± 4.71 |
| posterior ocular region | retina-choroid [(μg/g-tissue)/(mg/device)] | 2.90 ± 1.05 | 2.65 ± 0.99 | 2.16 ± 1.24 |

As compared to Comparative Examples 3 and 4, Example 4 showed lower concentrations of ofloxacin in the external ocular tissue (lacrimal fluid) and the anterior ocular tissues (cornea and aqueous humor), and the highest concentration of ofloxacin in the posterior ocular tissue (retina-choroid) among the three devices. Therefrom it is clear that a ring-shaped device containing a drug and worn on the scleral surface can suppress transfer of the drug released from the device to the external ocular tissue and anterior ocular tissue, and deliver the drug efficiently to the posterior ocular tissues.

Experimental Example 5

Production of Ring-shaped Device (Production Method of Ring-shaped Device)

Example 5

Scleral Ring

According to the method of Experimental Example 1, a ring-shaped device (scleral ring) was produced. The ring-shaped device had outer diameter A: 20 mm, inner diameter B: 13 mm, inner edge portion thickness: 0.13 mm, intermediate portion thickness: 0.34 mm, and outer edge portion thickness: 0.17 mm (thickness was measured in the same manner as in Experimental Example 2). In addition, the weight of the device after ofloxacin impregnation was 73 mg.

Experimental Example 6

Drug Transferability to Anterior Ocular Tissue and Posterior Ocular Tissue

[Test Device]

Example 5

Scleral Ring

Comparative Example 4

Corneal Lens

[Test Method]

Using the devices of Example 5 and Comparative Example 4, a test (n=3) was performed in the same manner as in Experimental Example 4.

[Results]

Table 3 shows the concentration of ofloxacin in each tissue as corrected by the ofloxacin content of each device. The ofloxacin content of each device was measured in the same manner as in Experimental Example 4 (n=1).

TABLE 3

| | | Example 5 (scleral ring) | Comparative Example 4 (corneal ring) |
|---|---|---|---|
| | ofloxacin content of device [mg/device] | 0.56 | 0.33 |
| anterior ocular region | aqueous humor [(μg/mL-tissue)/(mg/devise)] | 5.50 ± 1.20 | 23.84 ± 0.27 |
| posterior ocular region | retina-choroid [(μg/g-tissue)/(mg/devise)] | 7.34 ± 3.71 | 1.21 ± 0.76 |

The number values show mean±standard deviation.

As compared to Comparative Example 4, Example 5 showed lower concentration of ofloxacin in the anterior ocular tissue (aqueous humor) and higher concentration of ofloxacin in the posterior ocular tissue (retina-choroid). Therefrom it is clear that a ring-shaped device containing a drug and worn on the scleral surface can suppress transfer of the drug released from the device to the anterior ocular tissue, and deliver the drug efficiently to the posterior ocular tissues.

Moreover, as compared to Example 4 in Experimental Example 4, Example 5 showed improved drug transferability to the posterior ocular tissues.

Production Example 1

Ring-shaped Device

According to the method of Experimental Example 1, a ring-shaped device (scleral ring) is produced. The ring-shaped device has outer diameter A: 20 mm, inner diameter B: 13 mm, inner edge portion thickness: 0.05 mm, intermediate portion thickness: 0.34 mm, and outer edge portion thickness: 0.05 mm (thickness is measured in the same manner as in Experimental Example 2).

Production Example 2

Ring-shaped Device

According to the method of Experimental Example 1, a ring-shaped device (scleral ring) is produced. The ring-shaped device has outer diameter A: 20 mm, inner diameter B: 13 mm, inner edge portion thickness: 0.05 mm, intermediate portion thickness: 0.08 mm, and outer edge portion thickness: 0.05 mm (thickness is measured in the same manner as in Experimental Example 2).

INDUSTRIAL APPLICABILITY

According to the present invention, a ring-shaped device superior in the wearing comfort and intraocular stability, as well as a ring-shaped device capable of delivering a drug efficiently to posterior ocular tissues can be obtained.

This application is based on patent application Nos. 2009-028976 filed in Japan (filing date: Feb. 10, 2009) and 2009-228303 (filing date: Sep. 30, 2009), the contents of which are incorporated in full herein by this reference.

EXPLANATION OF SYMBOLS 1 curved thin film
2 opening (penetrating hole)
3 cut
4 clipping
10 device

The invention claimed is:

1. A device to be worn on a scleral surface,
wherein the device is made of a curved thin film having a ring shape, and the device has an opening to expose a cornea,
wherein one surface of the curved thin film forms a concave surface and another surface of the curved thin film forms a convex surface, and the concave surface and the convex surface have different curvatures,
wherein the curved thin film has an intermediate portion between an inner edge portion and an outer edge portion,
wherein the intermediate portion has a minimum thickness and a maximum thickness, and wherein the inner edge portion has a thickness within the range of 0.05-0.3 mm, the outer edge portion has a thickness within the range of 0.05-0.3 mm, the intermediate portion has a thickness within the range of 0.08-0.4 mm, the minimum thickness of the intermediate portion is not less than the thickness of the inner edge portion and is not less than the thickness of the outer edge portion, and the maximum thickness of the intermediate portion is greater by 0.03 mm or more than both the thickness of the inner edge portion and the thickness of the outer edge portion.

2. The device according to claim 1, wherein the inner edge portion has a thickness within the range of 0.1-0.3 mm, the outer edge portion has a thickness within the range of 0.15-0.3 mm, and the intermediate portion has a thickness within the range of 0.2-0.4 mm.

3. A device comprising a drug,
wherein the device is to be worn on a scleral surface,
wherein the device is made of a curved thin film having a ring shape, and the device has an opening to expose a cornea,
wherein one surface of the curved thin film forms a concave surface and another surface of the curved thin film forms a convex surface, and the concave surface and the convex surface have different curvatures,
wherein the curved thin film has an intermediate portion between an inner edge portion and an outer edge portion,
wherein the intermediate portion has a maximum thickness,
wherein the inner edge portion has a thickness within the range of 0.05-0.3 mm, the outer edge portion has a thickness within the range of 0.05-0.3 mm, the intermediate portion has a thickness within the range of 0.08-0.4 mm, the minimum thickness of the intermediate portion is not less than the thickness of the inner edge portion and is not less than the thickness of the outer edge portion, and the maximum thickness of the intermediate portion is greater by 0.03 mm or more than both the thickness of the inner edge portion and the thickness of the outer edge portion, and
wherein the curved thin film is impregnated with the drug.

4. The device according to claim 3, wherein the inner edge portion has a thickness within the range of 0.1-0.3 mm, the outer edge portion has a thickness within the range of 0.15-0.3 mm, and the intermediate portion has a thickness within the range of 0.2-0.4 mm.

5. A method of delivering a drug to posterior ocular tissues, comprising applying the device according to claim 3 on the scleral surface to transfer the drug contained in the device to posterior ocular tissues.

6. The device according to claim 3, wherein the drug is a therapeutic agent for a posterior ocular tissue disease.

* * * * *